(12) United States Patent
Zhang et al.

(10) Patent No.: US 6,551,312 B2
(45) Date of Patent: Apr. 22, 2003

(54) WIRELESS ELECTROSURGICAL DEVICE AND METHODS THEREOF

(75) Inventors: Ji Zhang, Burnaby (CA); Terence J. Gilhuly, Vancouver (CA); Samuel V Lichtenstein, Vancouver (CA)

(73) Assignee: Quantum Cor, Inc., Irvine, CA (US)

( * ) Notice: Subject to any disclaimer, the term of this patent is extended or adjusted under 35 U.S.C. 154(b) by 61 days.

(21) Appl. No.: 09/803,284

(22) Filed: Mar. 9, 2001

(65) Prior Publication Data
US 2002/0128646 A1 Sep. 12, 2002

(51) Int. Cl.[7] .................. A61B 19/04; A61B 18/08; A61B 18/12
(52) U.S. Cl. .............. 606/41; 606/28; 606/30; 606/42; 607/150
(58) Field of Search ............... 606/1, 34, 41, 606/32, 27–31, 37, 42, 45, 49; 607/150

(56) References Cited

U.S. PATENT DOCUMENTS

| | | | | |
|---|---|---|---|---|
| 3,845,771 A | * | 11/1974 | Vise | 606/49 |
| 4,510,939 A | * | 4/1985 | Brenman et al. | 128/639 |
| 4,765,343 A | * | 8/1988 | Brenman et al. | 128/639 |
| 4,878,493 A | * | 11/1989 | Pasternak et al. | 607/99 |
| 5,242,440 A | * | 9/1993 | Shippert | 606/30 |
| 5,792,138 A | | 8/1998 | Shipp | |
| 5,961,514 A | | 10/1999 | Long et al. | |
| 6,039,734 A | * | 3/2000 | Goble | 606/41 |
| 6,120,501 A | | 9/2000 | Long et al. | |
| 6,235,027 B1 | * | 5/2001 | Herzon | 606/51 |
| 6,423,059 B1 | * | 7/2002 | Hanson et al. | 606/41 |

FOREIGN PATENT DOCUMENTS

JP     2001-17385    *  1/2001

OTHER PUBLICATIONS

Zinder DJ, "Common myths about electrosurgery" Otolaryngol Head Neck Surg 2000; 123:450–5.
Kim DW, "Electric and laser energy for endoscopic surgery" Yonsei Med J 40(6): 536–544, 1999.
Weber PJ, et al. "Electrosurgical suspension apparatus" Dermatol Surg 2000; 26:142–145.

* cited by examiner

Primary Examiner—Joseph Pelham

(57) ABSTRACT

An improved wireless electrosurgery instrument comprising at least one surface electrical contact for contactably coupling the wireless instrument to a remote power source through a coupling mechanism, wherein the coupling mechanism comprises an insulated electrical conductor running through a surgeon's glove and/or a surgeon's gown.

23 Claims, 9 Drawing Sheets (A) User indication:

(a) Cut operation (b) Coagulation operation (B) Transmitter function:

(C) Receiver receives after coupling and amplifying:

(D) Receiver timing circuitry receives:

WIRELESS ELECTROSURGICAL DEVICE AND METHODS THEREOF

FIELD OF THE INVENTION

The present invention generally relates to improved electrosurgical devices and methods for use. More particularly, this invention relates to a remotely wired electrosurgical device for ablating, cutting, or coagulating tissues via a wireless instrument with high frequency energy.

BACKGROUND OF THE INVENTION

Electrosurgical devices are used in nearly every operating room today. Electrocautery systems are used as a substitute for a mechanical, sharp blade for the purposes of cutting tissue or coagulation. An electrosurgical device may be used in open-chest surgeries or in minimally invasive endoscopic operations. Known electrosurgical instruments include, for example, monopolar blades, bipolar forceps, bipolar scissors, monopolar hooks, monopolar scissors, bipolar endocutters, electric coagulators, or the like. Each of those instruments has an electrosurgical end effector which is adapted to treat tissue through application of electrosurgical energy to tissue which is brought in contact with the electrosurgical end effector. Most known electrosurgical instruments are connected by electrical cords or wires to electrosurgical generators.

In general, the terms for electrosurgery, electrocautery, radiosurgery, diathermy, endothermy and radiofrequency heating have all been used to refer to tissue application of radiofrequency electricity to obtain a desired effect. In its classic meaning, electrocautery is defined as the use of electricity to heat an object, which is then touched to the tissue to singe vessels. Electrosurgery usually uses radiofrequency electricity to generate heat in the tissue itself rather than applying heat from an outside source.

It has been noticed by surgeons that the standard electrocautery instrument is inconvenient for them to use due to the attached wire or electrical cord. The wire could become tangled on the cautery instrument or on another object, and can be troublesome to their hand motion, make cautery awkward and less efficient. The electrical cord is also a nuisance in that it requires monitoring and careful placement to ensure that it remains sterile during surgical operations. Some surgeons have developed innovative methods for hanging or suspending the electrical cords, facilitating use of the electrosurgical devices and reducing the interference of the cords. For example, Weber et al. described a novel, yet simple, electrosurgical suspension apparatus that facilitate the performance of excision and repair, Mohs micrographic surgery, cosmetic surgery, and other forms of dermatologic surgery in Dermatology Surgery 2000;26:142–145.

It has been noted that certain tasks, such as laparoscopic cautery, would benefit from the application of cautery without the use of another instrument such as cautery obturator. Furthermore, a surgeon has noted that he cannot always see as clearly as he would like while cutting in non-lapascopic surgeries.

The prior art of surgical cautery is mainly performed electrically with a monopolar or bipolar cautery instrument. The instrument transforms hospital available AC power into low current electricity, high frequency waveforms to cut through tissue and/or coagulate tissue. The attached electrical conducting wire or cord remains an unnecessary troublesome problem. This also applies to non-surgery electrical instruments.

An apparent form of the cordless electrosurgical device is a battery-powered cautery instrument or handpiece. U.S. Pat. No. 5,792,138 to Shipp discloses a cordless battery-operated electrocautery unit for use in surgical procedures. Though the battery-powered handpiece shows cordless advantages, the power may drift and the cautery efficiency demands constant battery exchange or recharge. The battery itself also increases the weight of the instrument.

Another alternative form of the cordless electrosurgical instruments is a specifically designed trocar or trocar adapter. U.S. Pat. No. 5,961,514 to Long et. al. discloses a cordless electrosurgical instrument that is adapted to fit through a trocar which includes an electrosurgical adapter with at least a first electrical contact positioned in and extending axially along the elongated aperture, an electrical conductor, an external conductor, an outer housing and an electrical cord attached to it.

Electrosurgical generators supply electrical energy to the electrosurgical instruments through electrical cords. The cordless electrosurgical instrument as disclosed in U.S. Pat. No. 5,961,514 still requires a specially designed trocar having an attached electrical cord connected to a generator. Furthermore, the Long et. al. device needs an extra hand to engage the trocar or trocar adapter to the cordless instrument, which is not a contactably coupling technique and the device applies only to laparoscopic procedures.

Therefore, there is an unmet clinical need for integrating the power and signal source into a surgeon's gloves and/or gown as a remotely wired system while the actual cautery or ablation is done with a cordless instrument. The technology that is readily applicable on a wireless instrument could apply to any cautery instrument, ablation handpiece, any electrosurgery apparatus, or the like.

SUMMARY OF THE INVENTION

In general, it is an object of the present invention to provide a wireless electrosurgical device system for contactably coupling a wireless instrument to a remote power source. In one preferred embodiment, a remotely wired electrosurgical device system comprises a wireless instrument and a remote power source, wherein the wireless instrument comprises at least one surface electrical contact for contactably coupling the wireless instrument to the remote power source through a coupling mechanism. In another preferred embodiment, the coupling mechanism further comprises a glove having at least one electrically conductive patch zone located at an outer surface of the glove for contactably coupling the wireless instrument to the remote power source. The glove may further comprise an insulated glove conductor having a first end and a second, the first end of said insulated glove conductor being connected to one of the at least one electrically conductive patch zone of the glove and the second end of said insulated glove conductor being coupled to said remote power source.

In another embodiment, the device system further comprises a gown having an insulated gown conductor, the insulated gown conductor being positioned between the second end of the insulated glove conductor and said remote power source.

In still another embodiment, the wireless instrument further comprises a signal transmitter and the remote power source comprises a switching/receiver unit, wherein signals transmitted from said transmitter are received by the switching/receiver unit adapted for switching the power on. The signals may be transmitted either by short range radiofrequency transmission method or by capacitively coupled signal transmission method.

A method for performing a cordless electrosurgery operation, the method comprises contactably coupling a wireless instrument and a remote power source through a coupling mechanism on a surgeon's glove, a surgeon's gown, and the like.

BRIEF DESCRIPTION OF THE DRAWINGS

Additional objects and features of the present invention will become more apparent and the invention itself will be best understood from the following Detailed Description of the Exemplary Embodiments, when read with reference to the accompanying drawings.

DETAILED DESCRIPTION OF THE EXEMPLARY EMBODIMENTS

Referring to FIGS. 1 to 9, what is shown is an embodiment of the wireless electrosurgical device system comprising a wireless instrument, a coupling mechanism and a remote power source.

Figure 1:
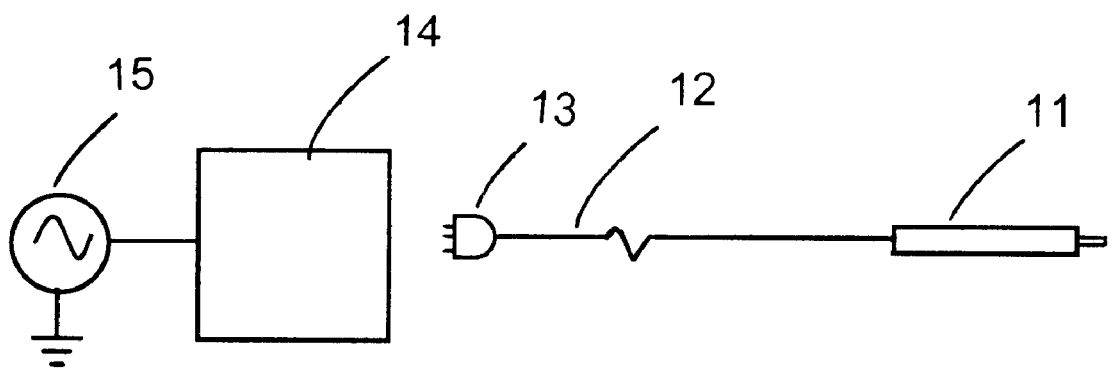
FIG. 1 is an example of prior art electrosurgical device systems.

FIG. 1 shows an example of prior art electrosurgical device systems. Currently surgical cautery is mainly performed electrically with a monopolar cautery instrument, though bipolar cautery instruments are also used occasionally. The prior art instrument transforms hospital available AC power (100 to 250VAC approximately, dependent upon the country) into low current electricity, high frequency (including radiofrequency) waveforms to cut through and/or to coagulate tissue. The cutting and coagulating waveforms are delivered to the tissue through a cautery scalpel that plugs into the cautery power supply through a standard cautery interface. There is a switch on the cautery scalpel that a practitioner or surgeon uses to close the appropriate circuit for either cutting or coagulation. Typically, a wired cautery instrument 11 with its attached wire or electrical cord 12 and a connector 13 is plugged into a standard electrosurgery power supply (EPSU) 14 or indirectly connected to a remote power source 15. The standard electrosurgery power supply in this invention can be a high frequency power generator, such as a radiofrequency generator.

Figure 2:
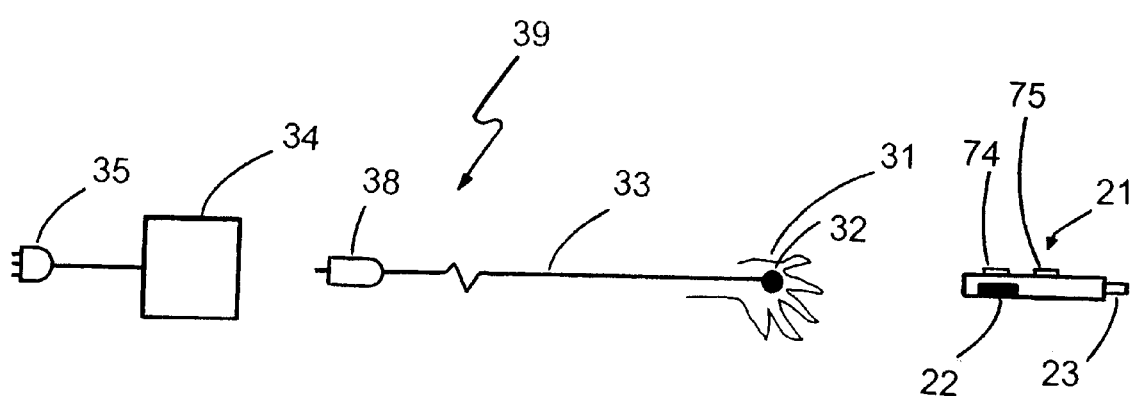
FIG. 2 is a wireless electrosurgery instrument system constructed in accordance with the principles of the present invention.

FIG. 2 shows a wireless electrosurgery instrument system constructed in accordance with the principles of the present invention. The remotely wired electrosurgical device system comprises a wireless electrosurgery instrument 21 having a transmitter and a remote power source 15, wherein the wireless instrument 21 comprises an end effector 23 and at least one surface electrical contact 22 for contactably coupling the wireless instrument to the remote power source through a coupling mechanism 39. The term "contactably coupling" as referred in this invention is defined as coupling two electrical contact elements by contacting without plugging or connection. U.S. Pat. No. 5,961,514 discloses a cordless electrosurgical instrument that uses a trocar or trocar adapter as a coupling element for power supply, wherein the trocar or trocar adapter needs to plug into the electrosurgery instrument using an extra hand. Loose wires from the trocar adapter become a troublesome problem to the surgeon. On the contrary, the wireless instrument of the present invention has neither loose wires to interfere with the surgeon's hand motions nor does it contain a battery-pack.

Figure 3:
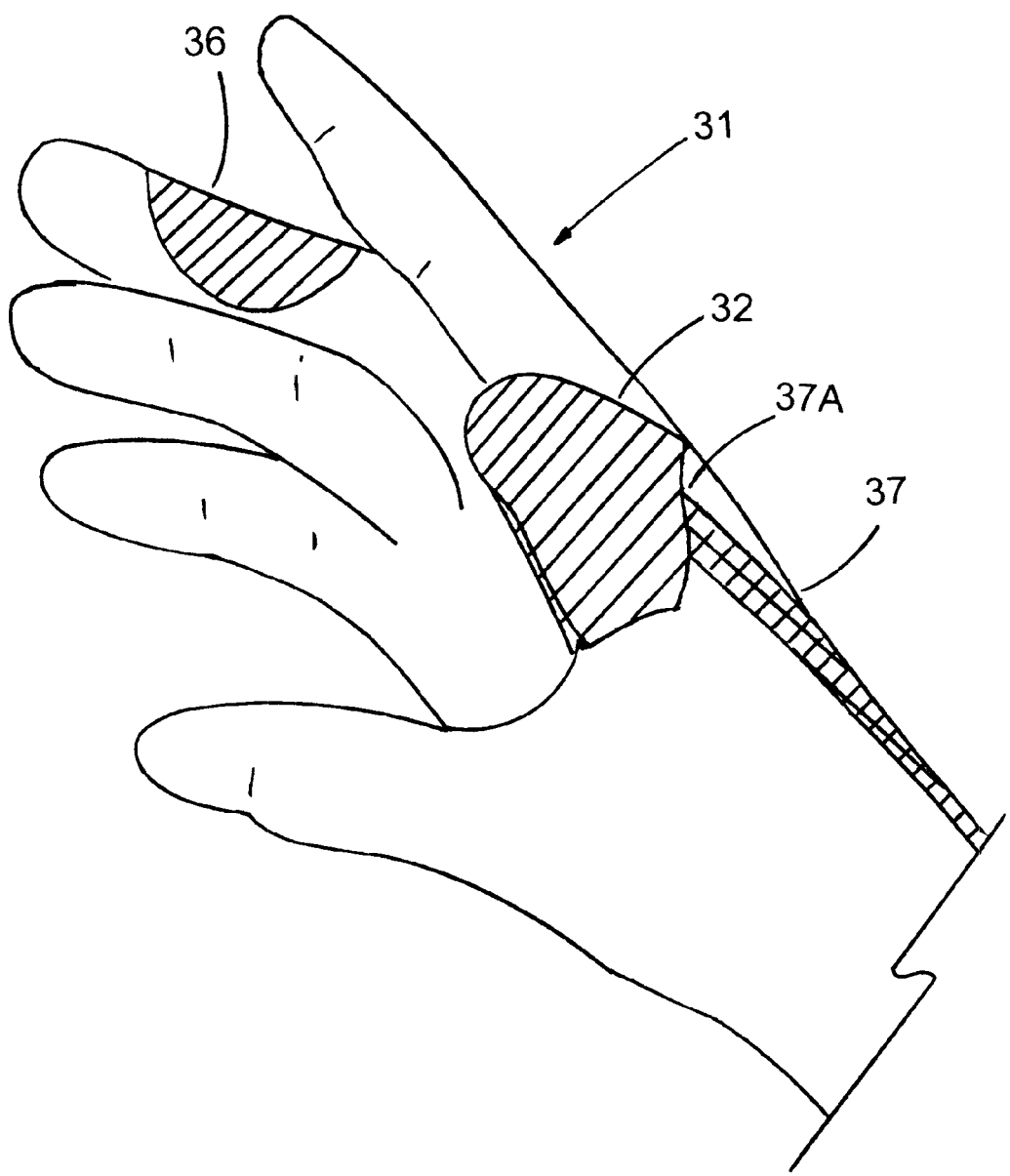
FIG. 3 is a surgeon's glove serving as a coupling mechanism adapted for coupling the wireless electrosurgery instrument to a remote power source.

In one embodiment, the coupling mechanism 39 may comprise a surgery glove 31 to be worn by a surgeon for performing electrosurgery on a patient and a plug 38 to be connected to a switching/receiver 34, which is electrically connected through an end plug 35 to and becomes an additional component of the generator 14 and remote power source 15. In one preferred embodiment, the switching/receiver may be enclosed within an EPSU 14 or otherwise stand-alone. The surgery glove 31 has at least one electrically conductive patch zone 32 located at an outer surface of the glove for "contactably coupling" the wireless instrument to the remote power source through an attached conductor wire 33. As shown in FIG. 3 for an alternate bipolar electrocautery operation, a second electrically conductive patch zone 36 on the glove surface may be provided for contactably coupling a second of the at least one surface electrical contact 22 of the bipolar wireless instrument to the remote power source 15 as a returning conductor wire.

The wireless instrument 21 may also comprise an end effector 23, the end effector being electrically coupled to one of the at least one surface electric contact 22 through a first internal conducting wire within the instrument (not shown). Therefore, a complete circuit is established by a returning electrode 52 normally placed contactably under the patient and returning the current to the standard electrosurgery power supply unit (EPSU) 14. In a bipolar instrument, the end effector 23 further comprises a returning electrode which is connected through a second internal conducting wire within the instrument to a second of the at least one surface electrical contact 22 for contactably coupling the wireless instrument to the remote power source through the coupling mechanism 39. The coupling mechanism 39, that may comprise at least one conducting wire, may be disposable or sterilized for re-use.

The end effector may include the distal portion of an electrosurgery instrument, such as bipolar forceps, bipolar scissors, a monopolar hook, monopolar scissors, bipolar endocutters, an electric coagulator, or the like. The wireless instrument may be a scalpel that has an actuator mounted on said scalpel, the actuator being adapted for activating and deactivating the remote power source. Typically a small battery, such as an AAA size battery is optionally included in the end effector for light bulb use and for activating the feedback circuit.

FIG. 3 shows a surgeon's glove serving as a coupling mechanism 39 adapted for coupling the wireless electrosurgery instrument 21 to a remote power source 15. The glove may comprise at least an insulated glove conductor 37 having a first end 37A and a second end 37B, the first end of the insulated glove conductor being connected to the electrically conductive patch zone 32 of the glove and the second end of the insulated glove conductor being coupled to the remote power source optionally through the EPSU 14.

Figure 9:
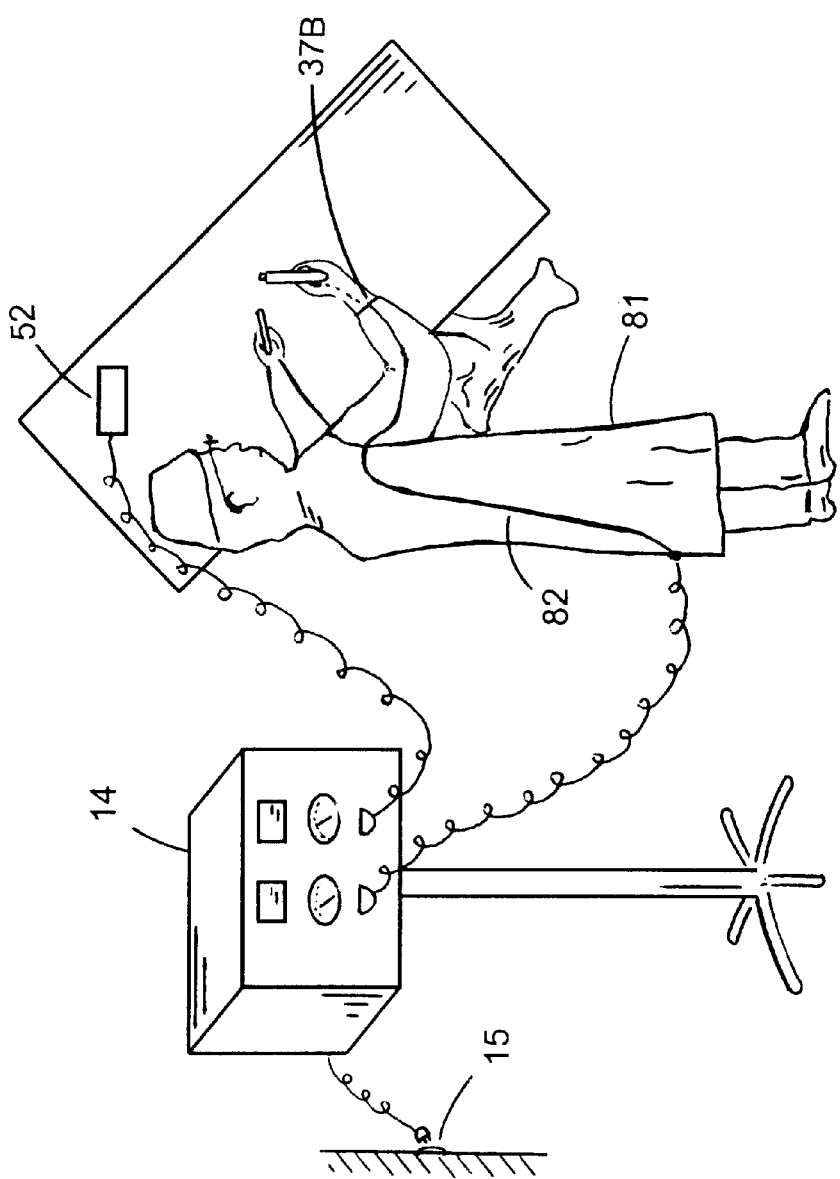
FIG. 9 is a perspective view of a simulated electrosurgery operation using the wireless electrosurgery device system of the present invention.

In one preferred embodiment, the device system further comprises a gown 81 (as shown in FIG. 9) having an insulated gown conductor 82, the insulated gown conductor being positioned between the second end 37B of the insulated glove conductor 37 and the remote power source 15 through the EPSU 14. For example, a monopolar electrosurgery instrument with cautery power delivered from a standard electrosurgery power supply unit to which the wireless instruments interfaced, to the wireless instrument through an insulated conductor attached to the surgeon's glove and gown. The insulated conductor could be built into the glove and/or gown or attached on top of it with glue, Velcro® tape or other fixation technique. The insulated gown conductor could be right-handed, left-handed or both-handed. Typically the insulated conducting wires could be placed inside or outside of the gloves or gown.

The remotely wired electrosurgical device system of the present invention consists at least one of the following elements: an end effector that may contact the tissue for electrosurgery operation in either a monopolar fashion or a bipolar fashion, a control circuitry, signaling mechanism, light and driving circuit, and power source.

Figure 4:
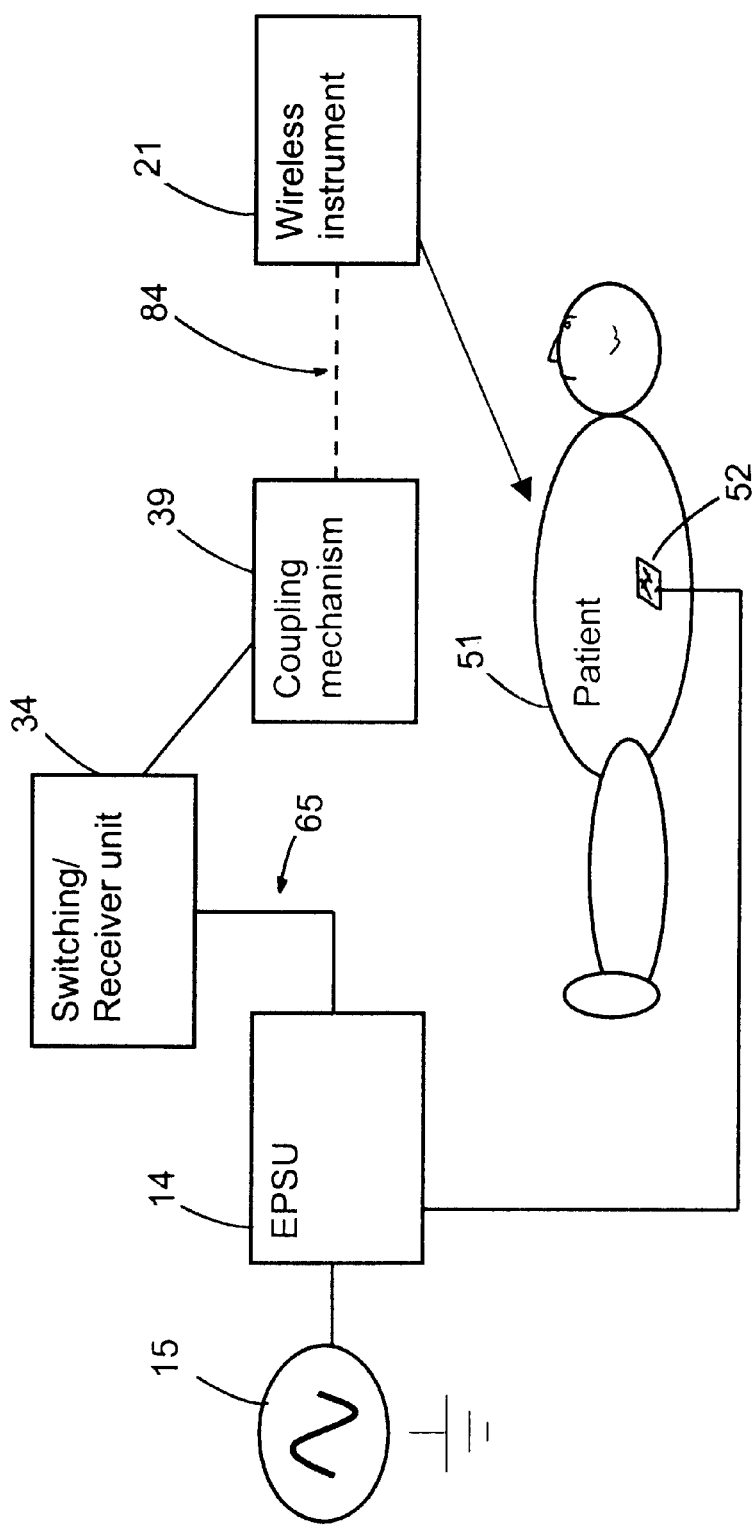
FIG. 4 is a schematic diagram illustrating the operating mode of the current wireless electrosurgery instrument system.

FIG. 4 shows a schematic diagram illustrating the operating mode of the current wireless electrosurgery instrument. A patient 51 has a returning electrode 52 for returning the electrical current back to the standard electrosurgery power supply unit (EPSU) 14. The EPSU has typically a plurality of ports to receive electricity from the power source and the return current from the patient's ground, as well as the output ports (for example, three banana jacks in the standard model) to which the coupling mechanism 39 interfaces. This same interface is used to connect to the switching/receiver unit 34. The wireless instrument 21 is remotely wired to the EPSU 14 by a coupling mechanism 39 in a "contactably coupling" fashion 84. The switching/receiver unit 34 receives the signal from a transmitter 71 mounted at or adjacent the wireless instrument 21.

Figure 5:
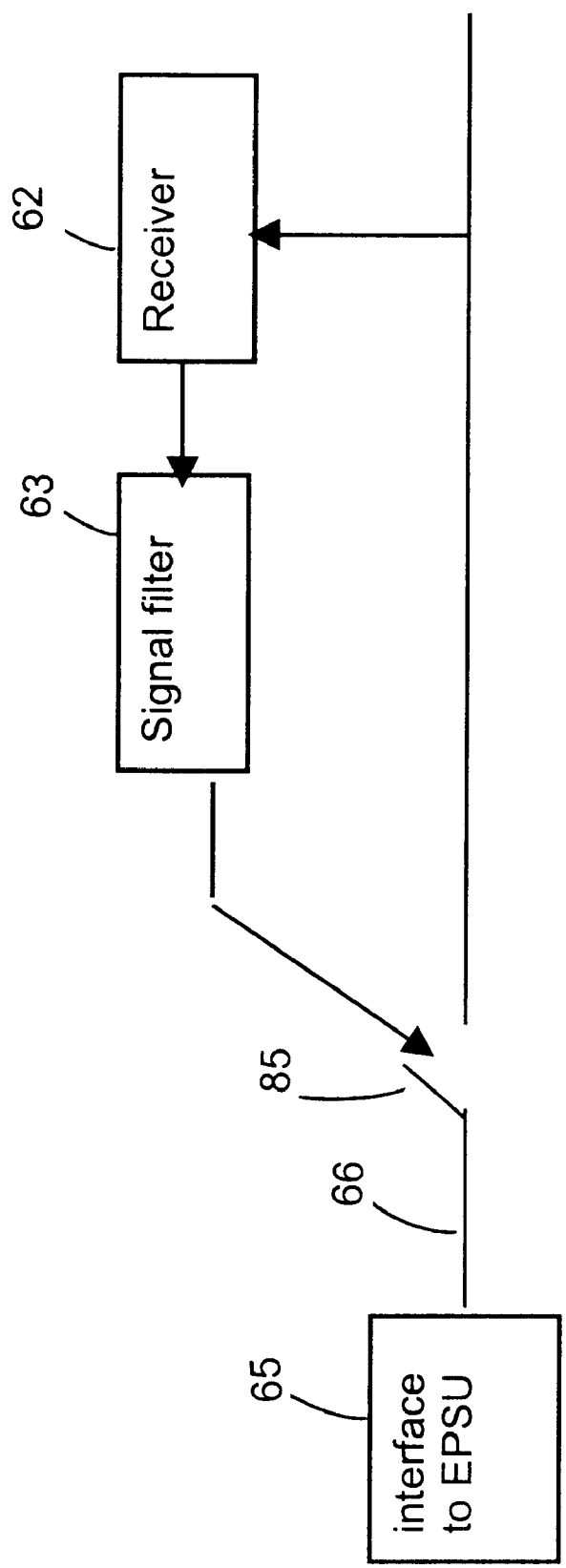
FIG. 5 is a switching/receiver unit for the wireless electrosurgery instrument.

The switching/receiver unit as shown in FIG. 5 comprises a receiver for the signals sent from the electronics in the wireless instrument either through RF or IR methods or along the line. The signals received are filtered through a signal filter 63 to activate the receiver relay 85 for power supply from the main power line 66 to the end effector. The interface 65 to EPSU is positioned between the EPSU 14 and the switching/receiver unit 34.

Figure 6:
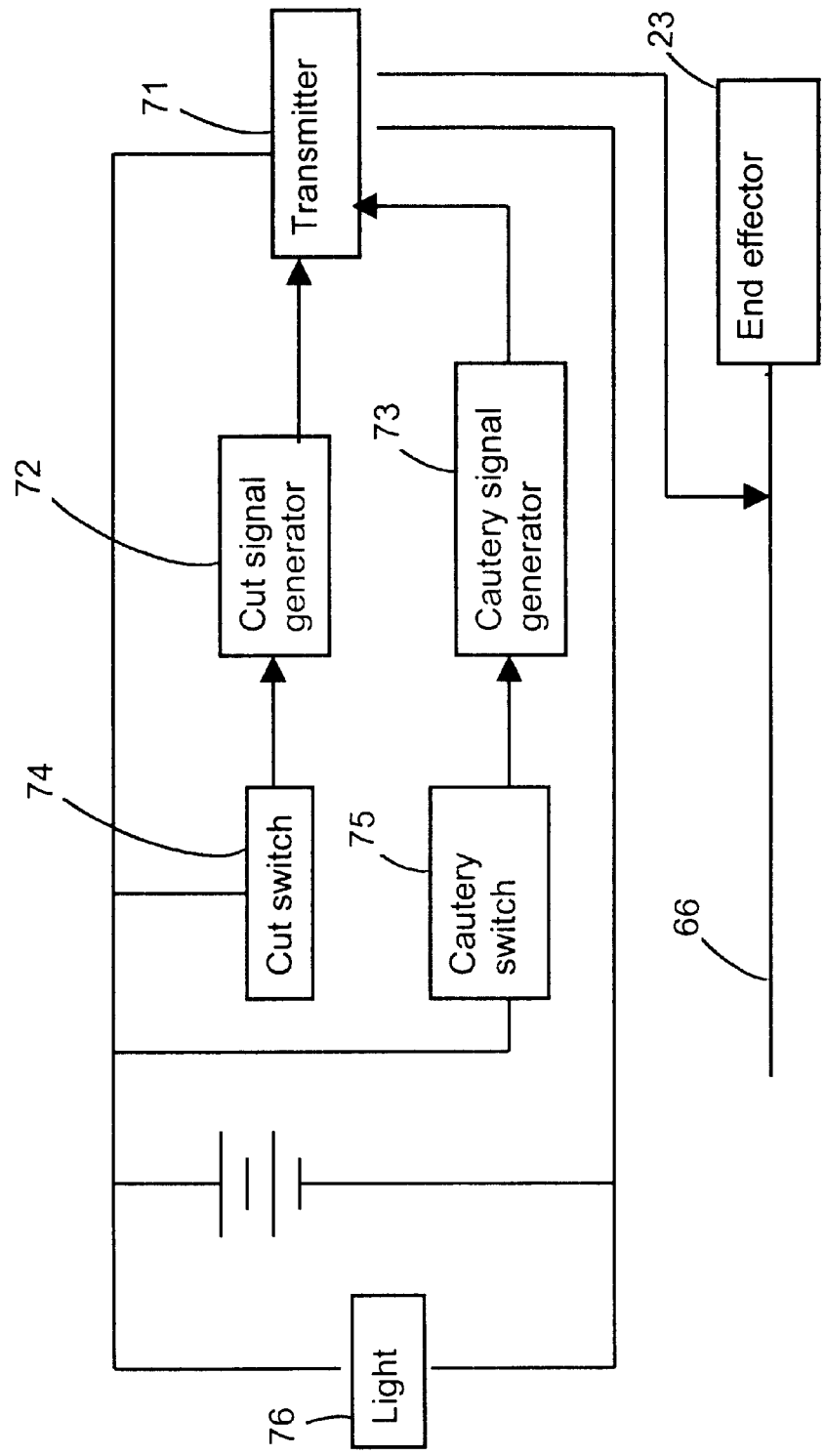
FIG. 6 is a detailed block diagram including an end effector for the wireless electrosurgery instrument.

FIG. 6 shows a detailed block diagram including an end effector 23 for the wireless electrosurgery instrument 21. In a preferred embodiment for dual cut and cautery functions, a transmitter subsystem 71 emits the signals for a desired cutting or cautery function to the switching/receiver unit 34. A light 76 is generally provided for the surgeon to better see the surgical site. After receiving and filtering the signal, the switching/receiver unit 34 then energize the circuits necessary to power oscillators attached to the main power line 66 for supplying the power to the end effector 23 of the wireless instrument 21. At least two of the push-button switches are located at the wireless instrument for different functions, such as cut, cautery or coagulation. In general, a cut switch 74 or a cautery switch 75 is depressed to activate a cut signal generator 72 or a cautery signal generator 73, followed by transmitting the signal to the switching/receiver unit 34 for power energizing.

Several communicating/signaling methods for activating the end effector of the wireless electrosurgery instrument are available. The communicating/signaling method of the present invention may be selected from a group consisting of (a) infrared transmission, (b) short range radio frequency signaling, and (c) monopolar end effector using capacitive coupling of signals. Other communication/signal transmission methods, such as voice activation, sound, ultrasound, light, laser, foot-switching activation, or the like are also applicable in the present invention.

Infra-red Transmission

The infrared transmission technique used infrared LEDs to transmit light pulses to perform the signaling and communication. Different signals for cutting, coagulating, inactive, or other function are made by varying the flashing frequency or other timing characteristics.

This communication could be done at very short range from one or several LEDs, possibly being arranged to form an optimized spreading of the light power, aimed at a receiver on the surgeon's glove. At the expense of power and the risk of line-of-sight blocking of the signal, this communication could also be done over a greater distance from a transmitter on top of the instrument to a receiver in a line-of-sight unobstructed location somewhere else in the operating suite.

The receiver (a phototransistor or other infra-red sensitive device) transduces the signal into something understandable by a microprocessor or other electronic circuitry. These electrical signals are then interpreted and the appropriate switches closed to turn on the desired electrosurgery operation.

This method of signaling has the limitations of interference by blocking of the signal forcing the transmitter to be close to the receiver, and through this limitation the necessity for extra wiring (including the receiver) being attached to the surgeon's arm.

Short Range RF Transmission

The short range RF transmission technique would work in much the same way but would instead use a RF transmitter located in the wireless electrosurgery instrument to transmit commands to a receiver. The receiver could be located on the surgeon's gown or elsewhere in the operating suite. The size and range of the antennae necessary would vary with the frequency permissible by the hospital and appropriate international standards. A good example of a system using short range RF transmission is a Bluetooth wireless mouse for a PC computer.

This would be an improvement over the infrared technique for its ability to communicate with an out-of-sight receiver, but would have the disadvantage of RF emissions in an operating room restricting the frequencies and the power levels being used. It would be possible to place the receiver somewhere on the operating table or close to the surgeon's hands for convenient signal transmission to the switching/receiver unit. In this application, transmitter must be a part of the wireless instrument. Antennae for receiving signals could be a second wire attached to the surgeon's gown.

Monopolar Cautery Using Capacitive Coupling of Signals

Another alternative is the one which integrates the signal and power delivery into the same conductor. This eliminates the requirement of a second set of wires on the user and the inconvenience of positioning them and maintaining appropriate orientations.

The transmitter in the wireless instrument in the user's hands and the receiver at the EPSU are now connected directly through a single conductor. The transmitter consists of circuitry to create voltage pulses of different time lengths depending on which task, for example, cut or coagulate, that the user wishes to perform.

These voltage pulses are sent along the single conductor to the receiver. Normally this would be ineffective as the transmitter being monopolar is effectively floating relative to the receiver. To get around this and create the illusion of a common basis (similar to ground but not electrically so), the signal is instead capacitively coupled to the receiver. The capacitor serves as a differentiator removing all DC content and passing only the AC. This transmitted signal is then reduced to two pulse spikes, one negative and one positive, framing the amount of time that the transmitter transmitted. The pulses are then massaged into regular electrical signals (e.g. at TTL levels) acceptable to timing circuitry, which calculates the time between the pulses and determines the user's intent. Once cut or coagulation is determined, the appropriate action is carried out.

Other transmission/communication methods are also applicable in the present invention. Two different frequencies are used to indicate the different operations. Receiver contains electronics to determine which frequency broadcast would still use capacitive coupling and switches to protect the electronics. One needs to choose frequencies wisely. It generally uses a frequency much greater than 60 Hz to avoid the 60 Hz hums. Shielded cable could be used for most of the length to limit radiation.

Operating Mode

Figure 7:
FIG. 7 is a dual function signals transmission and receiving sequence.
Figure 7:
Figure 7:
Figure 7:
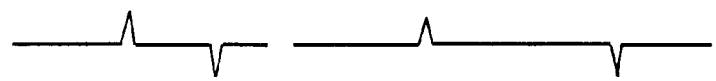
Figure 7:
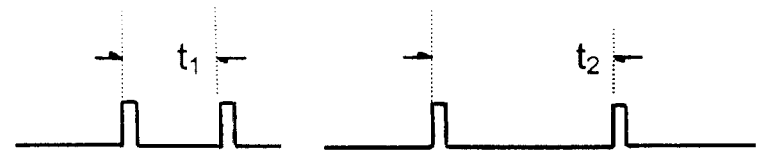

This operating mode is shown in FIG. 7 where the user indicates a cut and then a coagulate operation. "$t_1$" indicates the time for cut signal, and "$t_2$" indicates the time for coagulation signal. Note that these signals could be on the order of microseconds or less and as such the operations are separated as they would most likely not occur so close together in time.

The operating sequence as shown in FIG. 7 includes (A) user indication; (B) transmitter function; (C) receiver receiving after coupling and amplifying; and (D) receiver timing and processing circuitry receiving. The time required to indicate each operation mode could vary provided that there is still a sufficient difference in time length between the two signal types. After receiving and interpreting its orders, the selected operation would be carried out for a period of time, a number of multiples of the signaling time chosen to be long enough to achieve efficiency of operation and to remove noticeable and inconvenient delays from the user, and short enough so as to be turned off when no longer desired. This can be seen to form each operation into a packet of time consisting of signaling, delay to setup, operation, and delay to reset.

To avoid the problem of variation between clock oscillators (these are generally small, but crystal and other clock oscillators can have tolerances of a percent or two) creating skew problems or preventing proper use of the cautery due to inexact timing, the exact time taken for each of these pulses would be arranged between the transmitter and receiver in a calibration procedure at the start of any operation and before use. In the calibration procedure the transmitter sends to the receiver pulses for cutting, coagulation and for the amount of time that the operation will take place—the "on-time". The receiver receives each of these, measures them and stores for future comparison the amount of time each takes. This will facilitate coordination between the receiver and transmitter, removing the possibility of the transmitter circuitry being connected to (not isolated from) the conductor when the cautery waveform is applied.

It is important for the control circuitry to be isolated from the cautery waveforms due to the waveforms' high voltages (about 300 to 1500VDC) and high frequencies, which are enough to destroy circuit components. Although it is unlikely to be dangerous, it is probably best that the patient is isolated from the control signals. To evade unwanted exposure for the components and the patient, a method of separating the signals from the cautery was devised using electrically controlled mechanical relays and a timing scheme to isolate the two groups. This is shown in FIG. 8.

Figure 8:
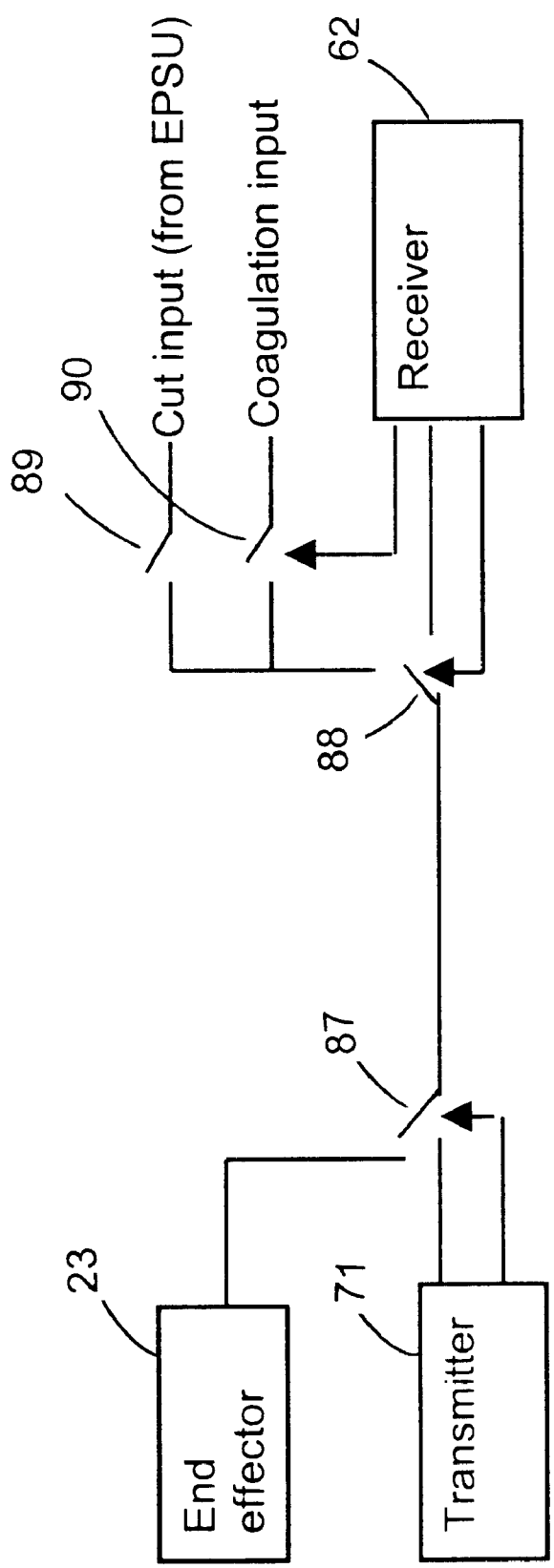
FIG. 8 is a block diagram of switches and basic system elements for dual cut and coagulation functions.

In FIG. 8, the transmitter 71 and receiver 62 are shown having outputs to various relays 87, 88, 89, 90. The transmitter controls a relay 87 that switches contact with the monopole between the transmitter and the cautery blade, an end effector 23. The receiver controls two relays: one relay that controls the type of cautery input (either cutting 89 or coagulation 90) and another relay 88 that switches monopole contact between the receiver and the cautery input.

Normally the relays are set to make the connection between the transmitter and receiver. After the user indicates their desired function and the transmitter transmits it, the transmitter activates relay 87 to connect up the end effector. Simultaneously, the valid timing signal is received at the receiver 62 and the receiver disconnects itself and connects one of the cut or coagulation inputs to the monopole direct to the end effector, and from there the signal passes into the patient.

After the pre-arranged "on time" (set during the calibration period), the receiver disconnects the cautery signal input and the transmitter reconnects itself to the monopole. The transmitter then waits for the user to give more input and the receiver waits for the transmitter to send a signal. Or should the user be holding the switch indicating an operation, the process begins again immediately. There is no confusion here for the receiver as to when to begin as the transmitter drives the process entirely.

It is unlikely but possible that noise could be substantial enough to be received as a pulse into the system. It would then set off a counter to await the next pulse. Thus there needs to be a method of determining when a pulse is legitimate or not. An error correction scheme could be set up using the time lengths stored from the calibration procedure as normal points and allow some variation in time from these.

FIG. 9 shows a perspective view of a simulated operation using the wireless electrosurgery device system of the present invention. A surgeon who holds a wireless electrosurgery instrument 21 has a coupling mechanism 39 comprising a glove 31 and/or a gown 81 of the present invention. The electrosurgery operation would become a complete circuit only when both the electrosurgery instrument contacts a patient who has a return electrode and the surgeon sends out a signal from the transmitter to activate the main power line through the EPSU 14.

The key advantage of the present invention over the prior art is its relative safety. The remotely wired electrosurgical device system of the present invention can only be activated by a surgeon or operator who has the coupling mechanism on his surgical glove and/or surgical gown. It is apparent that someone who picks up the instrument and depresses the transmitter button will not activate the instrument. This serves as a safety protection that is not available in other electrosurgical apparatus.

From the foregoing, it should now be appreciated that an improved wireless electrosurgery instrument having a coupling mechanism through a surgeon's glove and/or surgeon's gown has been disclosed. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. A remotely wired electrosurgical device system comprising a wireless instrument having a transmitter subsystem with a push-button switch mounted at or adjacent to said wireless instrument and a remote power source comprising a switching receiver unit for power energizing, the transmitter subsystem emitting a signal by depressing said push-button switch to the switching receiver unit for energizing the power source, wherein the wireless instrument comprises at least one surface electrical contact for contactably coupling the wireless instrument to the remote power source through a coupling mechanism.

2. The remotely wired electrosurgical device system of claim 1, wherein the coupling mechanism further comprises a glove having at least one electrically conductive patch zone located at an outer surface of the glove for contactably coupling the wireless instrument to the remote power source.

3. The remotely wired electrosurgical device system of claim 2, wherein the glove comprises an insulated glove conductor having a first end and a second end, the first end of said insulated glove conductor being connected to one of the at least one electrically conductive patch zone of the glove and the second end of said insulated glove conductor being coupled to said remote power source.

4. The remotely wired electrosurgical device system of claim 1, wherein the wireless instrument comprises an end effector, said end effector being electrically coupled to one of the at least one surface electric contact through a first internal conducting wire within the instrument.

5. The remotely wired electrosurgical device system of claim 1, wherein the remote power source is a radiofrequency power generator.

6. The remotely wired electrosurgical device system of claim 4, wherein the end effector is selected from a group consisting of monopolar blade, bipolar forceps, bipolar scissors, a monopolar hook, monopolar scissors, bipolar endocutters, and an electric coagulator.

7. The remotely wired electrosurgical device system of claim 1, wherein the wireless instrument is a scalpel that has an actuator mounted on said scalpel, the actuator being adapted for activating and deactivating the remote power source.

8. The remotely wired electrosurgical device system of claim 3, wherein the glove further comprises a second insulated glove conductor having a first end and a second end, the first end of said insulated glove conductor being connected to one of the at least one electrically conductive patch zone of the glove and the second end of said insulated glove conductor being coupled to said remote power source.

9. The remotely wired electrosurgical device system of claim 2, wherein the device system further comprises a gown having an insulated gown conductor, the insulated gown conductor being positioned between the second end of the insulated glove conductor and said remote power source.

10. The remotely wired electrosurgical device system of claim 1, wherein the wireless instrument further comprises a signal transmitter and the remote power source comprises a switching/receiver unit, and wherein signals transmitted from said transmitter are received by the switching/receiver unit adapted for switching the power on.

11. The remotely wired electrosurgical device system of claim 10, wherein the signals are transmitted by infrared transmission method.

12. The remotely wired electrosurgical device system of claim 10, wherein the signals are transmitted by short range RF transmission method.

13. The remotely wired electrosurgical device system of claim 10, wherein the signals are transmitted by capacitively coupled signal transmission method.

14. A method for performing a cordless electrosurgery operation, the method comprising contactably coupling a wireless instrument and a remote power source through a coupling mechanism mounted on a surgeon's glove, the wireless instrument comprising a transmitter subsystem emitting a signal for either cutting or cautery, wherein the transmitter subsystem sends out a signal to activate the power source depending on energy needs of cutting or cautery.

15. The method according to claim 14, wherein the coupling mechanism further comprises an electrically conductive patch zone located at an outer surface of the surgeon's glove for contactably coupling the wireless instrument to the remote power source.

16. The method according to claim 15, wherein the coupling mechanism further comprises a gown having an insulated gown conductor, the insulated gown conductor being positioned between the electrically conductive patch zone of the glove and said remote power source for contactably coupling the wireless instrument to the remote power source.

17. The method according to claim 14, wherein the signal is transmitted by infrared transmission method.

18. The method according to claim 14, wherein the signal is transmitted by short range RF transmission method.

19. The method according to claim 14, wherein the signal is transmitted by capacitively coupled signal transmission method.

20. The method according to claim 14, wherein the signal is by ultrasound signal transmission method.

21. The method according to claim 14, wherein the signal is transmitted by voice activation transmission method.

22. The method according to claim 14, wherein the step of sending out the signal is activated by foot-switching activation method.

23. A method for performing a cordless electrosurgery operation using an electrosurgical device system, wherein the device system comprises a wireless instrument having a transmitter subsystem with a push-button switch mounted at or adjacent to said wireless instrument and a remote power source comprising a switching receiver unit for power energizing, and wherein the wireless instrument comprises at least one surface electrical contact for contactably coupling the wireless instrument to the remote power source through a coupling mechanism, the method comprising:

contactably coupling the wireless instrument and the remote power source through the coupling mechanism mounted on a surgeon's glove;

depressing the push-button switch for sending out a signal from the transmitter subsystem to the switching receiver unit; and applying the wireless instrument to contact a patient for performing the cordless electrosurgery operation.

* * * * *